United States Patent [19]

Kaiser et al.

[11] 3,961,076

[45] June 1, 1976

[54] α-AMINOALKYL-4-HYDROXY-3-ALKYLSULFONYLMETHYLBENZYL ALCOHOLS HAVING β-ADRENERGIC STIMULANT ACTIVITY

[75] Inventors: Carl Kaiser, Haddon Heights, N.J.; Stephen T. Ross, Berwyn, Pa.

[73] Assignee: SmithKline Corporation, Philadelphia, Pa.

[22] Filed: July 18, 1975

[21] Appl. No.: 596,940

Related U.S. Application Data

[60] Division of Ser. No. 359,063, May 10, 1973, which is a continuation-in-part of Ser. No. 236,177, March 20, 1972, abandoned.

[52] U.S. Cl. ............................................... 424/330
[51] Int. Cl.$^2$ ...................................... A61K 31/135
[58] Field of Search .................................... 424/330

[56] References Cited

UNITED STATES PATENTS 3,775,479   11/1973   Bruderer et al.................... 424/330

*Primary Examiner*—Sam Rosen
*Attorney, Agent, or Firm*—Joseph A. Marlino; Richard D. Foggio; William H. Edgerton

[57] ABSTRACT

α-Aminoalkyl-4-hydroxy-3-alkylsulfonylmethylbenzyl alcohols having β-adrenergic stimulant activity, particularly as selected bronchodilators, are prepared from 4-hydroxyphenones by conversion to a 3-alkylsulfonylmethylphenone, bromination of these phenones and treatment of the resulting α-bromo derivatives with an N-benzyl secondary amine, followed by catalytic hydrogenation to remove the benzyl groups and reduce the ketone moiety.

10 Claims, No Drawings

α-AMINOALKYL-4-HYDROXY-3-ALKYLSULFONYLMETHYLBENZYL ALCOHOLS HAVING β-ADRENERGIC STIMULANT ACTIVITY

This is a division of application Ser. No. 359,063 filed May 10 1973 which is a continuation in part of Ser. No. 236,177 filed March 20 1972 now abandoned.

This invention relates to novel α-aminoalkyl-4-hydroxy-3-alkylsulfonylmethylbenzyl alcohols which have useful pharmacodynamic activity. More specifically, the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compounds of this invention have selective bronchodilating properties since they are active in (1) above at a dose lower than is required in (2) above resulting in a positive separation ratio.

The compounds of this invention are represented by the following general structural formula:

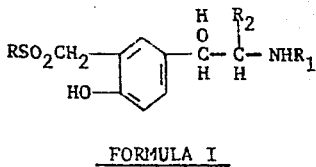

FORMULA I in which:

R represents lower alkyl of from 1 to 5 carbon atoms, straight or branched chain;

$R_1$ represents a branched chain lower alkyl group of from 3 to 5 carbon atoms, a cycloalkyl or cycloalkylmethyl group, the cycloalkyl moiety having from 3 to 6 carbon atoms, or

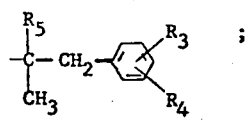

$R_2$ represents hydrogen, methyl or ethyl; and
$R_3$ and $R_4$ represent hydrogen, hydroxy or methoxy; and
$R_5$ represents hydrogen or methyl.

Preferred compounds of this invention are represented by formula I above when R is methyl; $R_1$ is isopropyl, t-butyl, cyclopropyl, cyclopentyl or 3,4-dimethoxyphenylisopropyl; and $R_2$ is hydrogen.

The compounds of this invention may be used in the form of a pharmaceutically acceptable acid addition salt having the utility of the free base. Such salts, prepared by methods well known to the art, are formed with both inorganic or organic acids, for example: maleic, fumaric, ascorbic, pamoic, succinic, bis-methylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexyl sulfamic, phosphoric and nitric acids.

Further the compounds of this invention contain at least one asymmetric carbon atom which is resolvable into d- and l- optical isomers. When $R_2$ in formula I is not hydrogen another asymmetric carbon atom is formed and these compounds (diastereoisomers) are designated as erythro and threo isomers which may be resolved as $d, l$ optical isomers. Unless otherwise specified in the description and accompanying claims, it is intended to include all isomers, whether separated or mixtures thereof.

A preferred compound of this invention is α-(t-butylaminomethyl)-4-hydroxy-3-(methylsulfonylmethyl)benzyl alcohol which relaxes the spontaneous tone of guinea pig tracheal ring preparation at an $ED_{50}$ of 0.0051 mcg/ml while increasing the rate of contraction of guinea pig right atria at an $ED_{25}$ of 8.28 mcg/ml. These activities give an absolute separation ratio of 1,620 which is a 3,340-fold improvement when compared to the corresponding activity of d, l-isoproterenol (absolute separation ratio = 0.5) in similar in vitro preparations.

The compounds of this invention are prepared as shown in the following sequence of reactions:

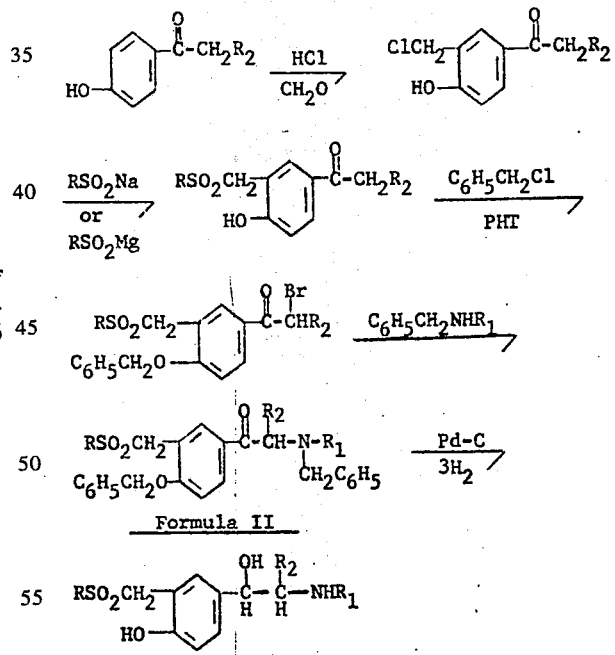

in which R, $R_1$ and $R_2$ are as defined in Formula I.

Thus, as shown above, a 4-hydroxyphenone is chloromethylated with formaldehyde and hydrochloric acid and is treated with the sodium or magnesium salt of an alkylsulfinic acid to yield the alkylsulfonylmethyl derivative. The latter is brominated and the resultant α-bromophenone is reacted with an N-benzylamine to give the corresponding α-benzylaminophenone. This derivative is hydrogenated catalytically, preferably with palladium-on-carbon, to give the debenzylated alkylsulfonylmethylbenzyl alcohol product.

It will be appreciated that the aminoketone derivatives of formula II in the above reaction sequence are useful intermediates and as such form a part of this invention.

The compounds of this invention may be administered orally or parenterally in conventional dosage unit forms such as tablets, capsules, injectables, aerosols, or the like, by incorporating the appropriate dose of a compound of formula I with carriers according to accepted pharmaceutical practices.

Preferably a compound or an acid addition salt thereof is administered orally to an animal organism in a tablet or capsule comprising an amount sufficient to produce $\beta$-adrenergic stimulant activity. Each dosage unit will contain the active ingredient in an amount of about 1 mg. to about 40 mg., preferably from about 3 mg. to about 20 mg. Advantageously equal doses will be administered 2 to 4 times daily with the daily dosage regimen being about 2 mg. to about 160 mg., preferably from about 6 mg. to about 80 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose of about 100 mcg. to about 650 mcg., administered once or twice at a time as needed.

The foregoing is a general description of how to prepare the compounds of this invention. The following examples illustrate the preparation of specific compounds having $\beta$-adrenergic stimulant activity. However, this should not be construed as a limitation of the invention since appropriate variations in the starting materials will produce other products set forth hereinabove.

EXAMPLE 1

To a mixture of 260 cc. of 37% formaldehyde and 1800 cc. of concentrated hydrochloric acid is added 100 g. of p-hydroxyacetophenone at a temperature of about 45° C. The mixture is maintained at 50° C. for two hours, filtered, and washed with water to give 3-chloromethyl-4-hydroxyacetophenone, m.p. 154° C. dec.

A mixture of 40 g. of 3-chloromethyl-4-hydroxyacetophenone and 26 g. of magnesium methyl sulfinate in 500 ml. of ethanol is refluxed with stirring for 3 hours. The reaction mixture is then concentrated in vacuo. The resultant oil is redissolved in chloroform and washed with water. The chloroform is dried and evaporated to give 4-hydroxy-3-methylsulfonylmethylacetophenone, m.p. 206.5–208.5°C.

A mixture of 14.0 g. of 4-hydroxy-3-methylsulfonylmethylacetophenone, 9.3 g. of potassium carbonate, 7.8 ml. of benzyl chloride and a catalytic amount of sodium iodide in 250 ml. of acetone and 250 ml. of water is refluxed with stirring for 16 hours. The acetone is removed and the aqueous phase is extracted with chloroform, washed with water, dried and evaporated to yield an oil which is recrystallized in isopropyl alcohol to give crystalline 4-benzyloxy-3-methylsulfonylmethylacetophenone, m.p. 94°–97° C.

To a stirred solution of 7.7 g. of 4-benzyloxy-3-methylsulfonylmethylacetophenone and 2.15 g. of 2-pyrrolidone in 300 ml. of tetrahydrofuran is added 12.5 g. of pyrrolidone hydrotribromide (PHT) and the stirring is continued for 56 hours at room temperature. The mixture is filtered and the filtrate concentrated in vacuo to give an oil which crystallizes upon standing. The crystals are redissolved in chloroform. The chloroform solution is washed with water, dried and concentrated to yield a solid which is recrystallized from acetonitrile to give 4-benzyloxy-$\alpha$-bromo-3-methylsulfonylmethylacetophenone, m.p. 143–144°C. The latter (100 g.) is dissolved in 1 l. of acetonitrile and 82 g. of N-benzyl-N-t-butylamine is added. The mixture is stirred and refluxed for four hours, cooled and diluted with ether. Crystalline N-benzyl-N-t-butylamine hydrobromide is filtered. The filtrate is acidified with ethereal hydrogen chloride and ether is added to give 4-benzyloxy-$\alpha$(N-benzyl-N-t-butylamino)-3-(methylsulfonylmethyl)acetophenone hydrochloride, m.p. 152–154°C.

A mixture of 20 g. of 4-benzyloxy-$\alpha$(N-benzyl-N-t-butylamino)-3-(methylsulfonylmethyl)acetophenone hydrochloride, 10 g. of 5% palladium-on-carbon and 125 ml. of ethanol is hydrogenated on the Parr apparatus at room temperature, using an initial hydrogen pressure of 60 psi. The reaction mixture is filtered and the filtrate is concentrated in vacuo. The residue is crystallized with ether-ethanol to yield $\alpha$-(t-butylaminomethyl)-4-hydroxy-3-(methylsulfonylmethyl)benzyl alcohol hydrochloride, m.p. 219–220°C.

EXAMPLE 2

Similarly, refluxing a solution of 3-chloromethyl-4-hydroxyacetophenone with sodium ethyl sulfinate or sodium butylsulfinate in ethanol and proceeding with the ensuing reactions as described above yields the corresponding $\alpha$-(t-butylaminomethyl)-4-hydroxy-3-(ethylsulfonylmethyl)benzyl alcohol hydrochloride or $\alpha$-(t-butylaminomethyl)-4-hydroxy-3-(butylsulfonylmethyl)benzyl alcohol hydrochloride.

EXAMPLE 3

Employing p-hydroxypropiophenone and p-hydroxybutyrophenone as the starting materials respectively and continuing as described in Example 1 yields $\alpha$-(1-t-butylaminoethyl)-4-hydroxy-3-(methanesulfonylmethyl)benzyl alcohol and $\alpha$-(1-t-butylaminopropyl)-4-hydroxy-3-(methylsulfonylmethyl)benzyl alcohol hydrochloride.

EXAMPLE 4

Following the procedures outlined in Example 1, 4-benzyloxy-α-bromo-3-methanesulfonylmethylacetophenone is condensed with N-benzylisopropylamine. Similar hydrogenation over palladium-on-carbon gives α-isopropylaminomethyl-4-hydroxy-3-(methylsulfonylmethyl)benzyl alcohol.

Reacting α-bromo-4-benzyloxy-3-methylsulfonylmethyl)-acetophenone with N-benzyl-3,4-dimethoxyphenylisopropylamine followed by hydrogenation yields the product α-[2-(3,4-dimethoxyphenyl)methylethylaminomethyl]-4-hydroxy-3-(methylsulfonylmethyl)benzyl alcohol.

Similarly, employing N-benzylcyclopropylmethylamine in the above reaction followed by hydrogenation, there is obtained α-(cyclopropylmethylaminomethyl)-4-hydroxy-3-(methylsulfonylmethyl)benzyl alcohol.

Following the procedures outlined in Example 1, condensation of 4-benzyloxy-α-bromo-3-methylsulfonylmethylacetophenone with N-benzylcyclopentylamine followed by hydrogenation gives α-(cyclopentylaminomethyl)-4-hydroxy-3-(methylsulfonylmethyl)benzyl alcohol.

EXAMPLE 5

Following the procedures of Example 1, condensation of 4-benzyloxy-α-bromo-3-methylsulfonylmethylacetophenone with N-benzylphenylisopropylamine followed by hydrogenation yields α-(2-phenyl-1-methylethylaminomethyl)-4-hydroxy-3-(methylsulfonylmethyl)benzyl alcohol.

Similarly, reaction of the 4-benzyloxy-α-bromoacetophenone with 3,4-dibenzyloxyphenylisopropylamine yields as the final product α-[2-(3,4-dihydroxyphenyl)-1-methylethylaminomethyl]-4-hydroxy-3-(methylsulfonylmethyl)benzyl alcohol.

EXAMPLE 6

Employing the procedures of Example 1, 4-benzyloxy-α-bromo-3-methylsulfonylmethylacetophenone is reacted with N-benzyl-4-benzyloxyphenylisopropylamine which followed by hydrogenation gives α-[2-(4-hydroxyphenyl)-1-methylethylaminomethyl]-4-hydroxy-3-(methylsulfonylmethyl)benzyl alcohol.

EXAMPLE 7

Following the procedures outlined in Example 1, 4-benzyloxy-α-bromo-3-methanesulfonylmethylacetophenone is reacted with N-benzyl-4-methoxyphenyl-t-butylamine which followed by hydrogenation gives α-[2-(4-methoxyphenyl)-1,1-dimethylethylaminomethyl]-4-hydroxy-3-(methylsulfonylmethyl)-benzyl alcohol.

The alcohol is treated with hydrogen chloride in methanol-ether giving α-[2-(4-methoxyphenyl)-1,1-dimethylethylaminomethyl]-4-hydroxy-3-(methylsulfonylmethyl)benzyl alcohol hydrochloride as colorless crystals having a melting point of 180°–182°C.

Similarly employing N-benzylcyclobutylamine in the above reaction followed by hydrogenation and treating the resultant alcohol with hydrogen chloride in methanol-ether yields α-(cyclobutylaminomethyl)-4-hydroxy-3-methylsulfonylmethyl)benzyl alcohol hydrochloride having a melting point of 193°–194° C.

EXAMPLE 8

| Ingredients | Mg./Capsule |
| --- | --- |
| α-(t-butylaminomethyl)-4-hydroxy-3-(methylsulfonylmethyl)benzyl alcohol | 2.242* |
| Starch, U.S.P. | 50.78 |
| Lactose, U.S.P. | 142.00 |
| Magnesium Stearate, U.S.P. | 3.00 |

*Equivalent to 2.0 mg. of free base

All the ingredients are thoroughly mixed and placed in a hard gelatin capsule.

One capsule is taken three times a day.

EXAMPLE 9

| Aerosol Spray Ingredients | Mg./Spray |
| --- | --- |
| α-(t-butylaminomethyl)-4-hydroxy-3-(methylsulfonylmethyl)benzyl alcohol | 0.3363* |
| Sorbitan Trioleate | 0.3000 |
| Freon 11 (Trichloromonofluoromethane, N.F.) | 10.0000 |
| Freon 12 (Dichlorodifluoromethane, N.F.) | 14.8000 |
| Freon 114 (Dichlorotetrafluoroethane, N.F.) | 12.2000 |

*Equivalent to 300 mcg. free base/spray

The above ingredients are placed in an aerosol spray dispensing system and result in the above indicated dose per spray.

What is claimed is:

1. A pharmaceutical composition having β-adrenergic stimulant activity in dosage unit form comprising a pharmaceutical carrier and an effective amount of a chemical compound of the formula:

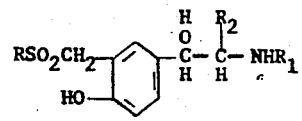

or a pharmaceutically acceptable acid addition salt of said compound, wherein:

R is straight or branched chain lower alkyl of from 1 to 5 carbon atoms;

$R_1$ is branched chain lower alkyl of from 3 to 5 carbon atoms, cycloalkyl or cycloalkylmethyl, the cycloalkyl moiety having from 3 to 6 carbon atoms, or

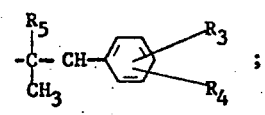

$R_2$ is hydrogen, methyl or ethyl;

$R_3$ and $R_4$ are hydrogen, hydroxy, or methoxy, and $R_5$ is hydrogen or methyl.

2. A pharmaceutical composition according to claim 1 in which R is methyl.

3. A pharmaceutical composition according to claim 2 in which $R_2$ is hydrogen.

4. A pharmaceutical composition according to claim 3 in which $R_1$ is t-butyl, being the compound α-(t-butylaminomethyl)-4-hydroxy-3-(methylsulfonylmethyl)benzyl alcohol.

5. A pharmaceutical composition in accordance with claim 1 in which said compound is in the form of a hydrochloride salt.

6. The method of producing β-adrenergic stimulant activity which comprises administering internally to animals requiring bronchodilation an amount sufficient to produce said activity a chemical compound of the formula:

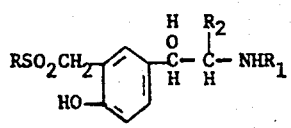

or a pharmaceutically acceptable acid addition salt of said compound, wherein:

R is straight or branched chain lower alkyl of from 1 to 5 carbon atoms;

$R_1$ is branched chain lower alkyl of from 3 to 5 carbon atoms, cycloalkyl or cycloalkylmethyl, the cycloalkyl moiety having from 3 to 6 carbon atoms, or

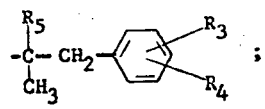

$R_2$ is hydrogen, methyl or ethyl;

$R_3$ and $R_4$ are hydrogen, hydroxy, or methoxy, and $R_5$ is hydrogen or methyl.

7. The method according to claim 6 in which R is methyl.

8. The method according to claim 7 in which $R_2$ is hydrogen.

9. The method according to claim 8 in which $R_1$ is t-butyl, being the compound α-(t-butylaminomethyl)-4-hydroxy-3-(methylsulfonylmethyl)benzyl alcohol.

10. A method in accordance with claim 6 in which said compound is in the form of a hydrochloride salt.

* * * * *